(12) United States Patent
Ward et al.

(10) Patent No.: US 11,058,318 B2
(45) Date of Patent: Jul. 13, 2021

(54) FLUID LEVEL DETERMINATION

(71) Applicant: Impedimed Limited, Pinkenba (AU)

(72) Inventors: Leigh Ward, Kenmore Hills (AU); Tim Essex, Clayfield (AU)

(73) Assignee: IMPEDIMED LIMITED, Pinkenba (AU)

( * ) Notice: Subject to any disclaimer, the term of this patent is extended or adjusted under 35 U.S.C. 154(b) by 589 days.

(21) Appl. No.: 15/744,650

(22) PCT Filed: Jul. 14, 2016

(86) PCT No.: PCT/AU2016/050616
§ 371 (c)(1),
(2) Date: Jan. 12, 2018

(87) PCT Pub. No.: WO2017/008118
PCT Pub. Date: Jan. 19, 2017

(65) Prior Publication Data
US 2018/0206759 A1    Jul. 26, 2018

(30) Foreign Application Priority Data
Jul. 16, 2015 (AU) .................. 2015902819

(51) Int. Cl.
*A61B 5/00* (2006.01)
*A61B 5/0537* (2021.01)
(Continued)

(52) U.S. Cl.
CPC .......... *A61B 5/0537* (2013.01); *A61B 5/1072* (2013.01); *A61B 5/1073* (2013.01);
(Continued)

(58) Field of Classification Search
CPC . A61B 5/0537; A61B 5/14532; A61B 5/7275; A61B 2018/00875; A61B 5/053;
(Continued)

(56) References Cited

U.S. PATENT DOCUMENTS 8,233,974 B2 * 7/2012 Ward .................. A61B 5/0537
600/547
8,271,079 B2 * 9/2012 Cha ...................... A61B 5/4869
600/547

(Continued)

FOREIGN PATENT DOCUMENTS

EP          2662020 A1    11/2013
WO    WO 2008/064426 A1    6/2008
(Continued)

OTHER PUBLICATIONS

International Search Report and Written Opinion dated Sep. 5, 2016 for Application No. PCT/AU2016/050616.
(Continued)

*Primary Examiner* — May A Abouelela
(74) *Attorney, Agent, or Firm* — Knobbe, Martens, Olson & Bear, LLP

(57) ABSTRACT

A method for use in determining fluid levels within a subject, the method including, in a processing device, determining at least one impedance value measured for the subject, determining physical dimensions for at least part of at least one segment of the subject, using the physical dimensions to determine a shape factor at least partially indicative of a shape of the at least one segment and calculating a fluid indicator indicative of the fluid levels in the segment at least in part using the at least one impedance value and the shape factor.

9 Claims, 9 Drawing Sheets

(51) Int. Cl.
*A61B 5/107* (2006.01)
*G06T 7/62* (2017.01)
*A61B 5/11* (2006.01)

(52) U.S. Cl.
CPC .......... *A61B 5/1079* (2013.01); *A61B 5/4881* (2013.01); *G06T 7/62* (2017.01); *A61B 5/1128* (2013.01); *A61B 5/6825* (2013.01); *A61B 5/6829* (2013.01); *A61B 2562/04* (2013.01); *G06T 2207/30004* (2013.01)

(58) Field of Classification Search
CPC ... A61B 5/1073; A61B 5/1079; A61B 5/4881; A61B 5/1072; A61B 5/6829; A61B 5/6825; A61B 5/1128; A61B 2562/04; C12Q 2563/116; C12Q 2565/607; G06T 7/62; G06T 2207/30004
USPC ..................... 600/300, 547; 702/65
See application file for complete search history.

(56) References Cited

U.S. PATENT DOCUMENTS

| | | | | |
|---|---|---|---|---|
| 9,724,012 | B2* | 8/2017 | Chetham | G16H 50/30 |
| 2007/0027402 | A1* | 2/2007 | Levin | A61B 5/4872 |
| | | | | 600/547 |
| 2007/0208233 | A1* | 9/2007 | Kovacs | A61B 5/1118 |
| | | | | 600/300 |
| 2008/0039700 | A1* | 2/2008 | Drinan | A61B 5/0537 |
| | | | | 600/301 |
| 2008/0270051 | A1* | 10/2008 | Essex | A61B 5/0537 |
| | | | | 702/65 |
| 2008/0287823 | A1* | 11/2008 | Chetham | A61B 5/0537 |
| | | | | 600/547 |
| 2008/0306400 | A1* | 12/2008 | Takehara | A61B 5/0537 |
| | | | | 600/547 |
| 2008/0319336 | A1* | 12/2008 | Ward | A61B 5/4878 |
| | | | | 600/547 |
| 2009/0043222 | A1* | 2/2009 | Chetham | A61B 5/4878 |
| | | | | 600/547 |
| 2010/0004515 | A1* | 1/2010 | Houben | G16H 50/20 |
| | | | | 600/300 |
| 2010/0152605 | A1* | 6/2010 | Ward | A61B 5/4878 |
| | | | | 600/547 |
| 2010/0168530 | A1* | 7/2010 | Chetham | A61B 5/0537 |
| | | | | 600/301 |
| 2011/0046505 | A1* | 2/2011 | Cornish | A61B 5/053 |
| | | | | 600/547 |
| 2011/0054343 | A1* | 3/2011 | Chetham | A61B 5/744 |
| | | | | 600/547 |
| 2011/0060239 | A1* | 3/2011 | Gaw | H04W 72/0486 |
| | | | | 600/547 |
| 2011/0087129 | A1* | 4/2011 | Chetham | A61B 5/7203 |
| | | | | 600/547 |
| 2011/0208084 | A1* | 8/2011 | Seoane Martinez | A61B 5/053 |
| | | | | 600/547 |
| 2011/0245711 | A1 | 10/2011 | Katra et al. | |
| 2011/0251513 | A1* | 10/2011 | Chetham | A61B 5/0537 |
| | | | | 600/547 |
| 2012/0203092 | A1* | 8/2012 | Sweeney | A61B 5/6831 |
| | | | | 600/390 |
| 2014/0276166 | A1* | 9/2014 | Drori | A61B 5/0531 |
| | | | | 600/529 |
| 2015/0105647 | A1* | 4/2015 | Katra | A61B 5/0537 |
| | | | | 600/391 |
| 2015/0309563 | A1* | 10/2015 | Connor | G06F 3/017 |
| | | | | 73/865.4 |
| 2015/0342539 | A1* | 12/2015 | Smits | A61B 5/00 |
| | | | | 600/300 |
| 2015/0377861 | A1* | 12/2015 | Pant | C12M 25/14 |
| | | | | 506/9 |
| 2016/0012749 | A1* | 1/2016 | Connor | G16H 20/60 |
| | | | | 600/13 |
| 2016/0150994 | A1* | 6/2016 | Smith | A61B 5/746 |
| | | | | 600/547 |
| 2017/0071500 | A1* | 3/2017 | Von Maydell | A61B 5/4869 |

FOREIGN PATENT DOCUMENTS

| | | |
|---|---|---|
| WO | WO 2008/128281 A1 | 10/2008 |
| WO | WO 2009/100491 A1 | 8/2009 |
| WO | WO 2010/051600 A1 | 5/2010 |
| WO | WO 2013/182985 A1 | 12/2013 |

OTHER PUBLICATIONS

De Lorenzo, A. et al., 'Predicting body cell mass with bioimpedance by using theoretical methods: a technological review', Journal of Applied Physiology, 1997, vol. 82, issue 5, pp. 1542-1558.

* cited by examiner

FLUID LEVEL DETERMINATION

RELATED APPLICATIONS

This application is a U.S. National Phase under 35 U.S.C. § 371 of the International Patent Application No. PCT/AU2016/050616, filed Jul. 14, 2016, and published in English on Jan. 19, 2017 as WO/2017/008118, which claims the benefit of Australian Patent Application No. 2015902819, filed Jul. 16, 2015, both of which are incorporated by reference in their entirety.

BACKGROUND OF THE INVENTION

The present invention relates to a method and apparatus for determining fluid levels in a biological subject using impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

"Predicting body cell mass with bioimpedance by using theoretical methods: a technological review" by A. DE LORENZO, A. ANDREOLI, J. MATTHIE, AND P. WITHERS, describes using a body shape factor to take into account that the human body is not a cylindrical shape when calculating body composition. Analysis of army personnel data has been previously determined a value of the body constant to be around 4.3, and this is generally treated as a constant. However, this is not representative of the general population and can result in incorrect calculations of body parameters when used for the general population.

SUMMARY OF THE PRESENT INVENTION

In one broad form the present invention seeks to provide a method for use in determining fluid levels within a subject, the method including, in a processing device:
a) determining at least one impedance value measured for the subject;
b) determining physical dimensions for at least part of at least one segment of the subject;
c) using the physical dimensions to determine a shape factor at least partially indicative of a shape of the at least one segment; and,
d) calculating a fluid indicator indicative of the fluid levels in the segment at least in part using the at least one impedance value and the shape factor.

Typically the method includes:
a) determining an impedance parameter value using the impedance measurement, the impedance parameter value being indicative of an impedance at zero frequency; and,
b) calculating the fluid indicator using the impedance parameter value.

Typically the method includes:
a) determining a number of impedance measurements, the number of impedance measurements including at least one impedance measurement at each of a number of measurement frequencies; and,
b) determining the impedance parameter value using the number of impedance measurements.

Typically the physical dimensions include a length and circumference of the at least one segment.

Typically the physical dimensions are at least one of:
a) measured for the subject; and,
b) derived from subject parameter values measured for the subject.

Typically the method includes:
a) determining subject parameters including:
  i) a height;
  ii) a weight;
  iii) an age; and,
  iv) a sex; and,
b) determining the physical dimensions using subject parameters.

Typically the method includes:
a) capturing at least one image of the subject; and,
b) measuring the physical dimensions from the at least one image.

Typically the method includes:
a) determining a silhouette of the subject from the at least one image; and,
b) measuring the physical dimensions from the silhouette.

Typically the method includes determining a whole of body fluid indicator by:
a) determining a whole of body impedance measurement;
b) determining physical dimensions for segments including at least:
  i) a torso;
  ii) an arm; and,
  iii) a leg;
c) using the physical dimensions to determine a whole body shape factor; and,
d) calculating the fluid indicator at least in part using the whole of body impedance measurement and the whole body shape factor.

Typically the fluid indicator is the volume of fluid and is calculated using the equation:

$$V = \left(K_B \frac{\rho H^2}{R}\right)^{1-x} \cdot V_{WB}^x$$

where: V is the volume of fluid
$K_B$ is the shape factor
$V_{WB}$ is the total body volume
$\rho$ is the resistivity of the fluid
H is the height of the subject
R is the impedance
x is a constant Typically shape factor is calculated using the equation:

$$K_B = \frac{1}{H^2}\left[\left(\frac{L_l}{C_l^2} + \frac{L_t}{C_t^2} + \frac{L_a}{C_a^2}\right)(2L_a C_a^2 + 2L_l C_l^2 + 2L_t C_t^2)\right]$$

where: $K_B$ is the shape factor
H is the height of the subject
$L_l$ is the length of the leg
$L_t$ is the length of the torso
$L_a$ is the length of the arm
$C_l$ is the circumference of the leg
$C_t$ is the circumference of the torso
$C_a$ is the circumference of the arm Typically the method includes determining a segmental fluid indicator indicative of the fluid volume of the at least one segment by:
 a) determining a segmental impedance measurement for at least one segment;
 b) determining physical dimensions for the at least one segment;
 c) using the physical dimensions to determine a segmental shape factor; and,
 d) calculating the fluid indicator at least in part using the segmental impedance measurement and the segmental shape factor.

Typically the fluid indicator is the volume of fluid and is calculated using the equation:

$$SV = \left(K_S \frac{\rho L^2}{R}\right)^{1-x} \cdot V_S^x$$

where: SV is the segmental fluid volume
$K_S$ is the segmental shape factor
$V_S$ is the segment volume
$\rho$ is the resistivity of the fluid
L is the segment length
R is the impedance
x is a constant Typically the fluid indicator is indicative of at least one of:
 a) extracellular fluid levels; and,
 b) intracellular fluid levels.

Typically the method includes, in the processing system:
 a) causing at least one drive signal to be applied to the subject using a signal generator;
 b) determining at least one sense signal measured across the subject using a sensor; and,
 c) determining at least one impedance value using an indication of the drive signal and the sensed signal.

In one broad form the present invention seeks to provide an apparatus for use in measuring fluid levels within a subject, the apparatus including:
 a) a signal generator that applies one or more drive signals to the subject using a first set of electrodes;
 b) a sensor that measures one or more sense electrical signals across a second set of electrodes applied to the subject; and,
 c) a processing device that:
  i) determines at least one impedance value measured for the subject using the drive and sense electrical signals;
  ii) determines physical dimensions for at least part of at least one segment of the subject;
  iii) uses the physical dimensions to determine a shape factor at least partially indicative of a shape of the at least one segment; and,
  iv) calculates a fluid indicator indicative of the fluid levels in the segment at least in part using the at least one impedance value and the shape factor.

It will be appreciated that the broad forms of the invention can be used in conjunction and/or independently, and reference to separate broad forms in not intended to be limiting.

BRIEF DESCRIPTION OF THE DRAWINGS

An example of the present invention will now be described with reference to the accompanying drawings, in which: —

DETAILED DESCRIPTION OF THE PREFERRED EMBODIMENTS

Figure 1:
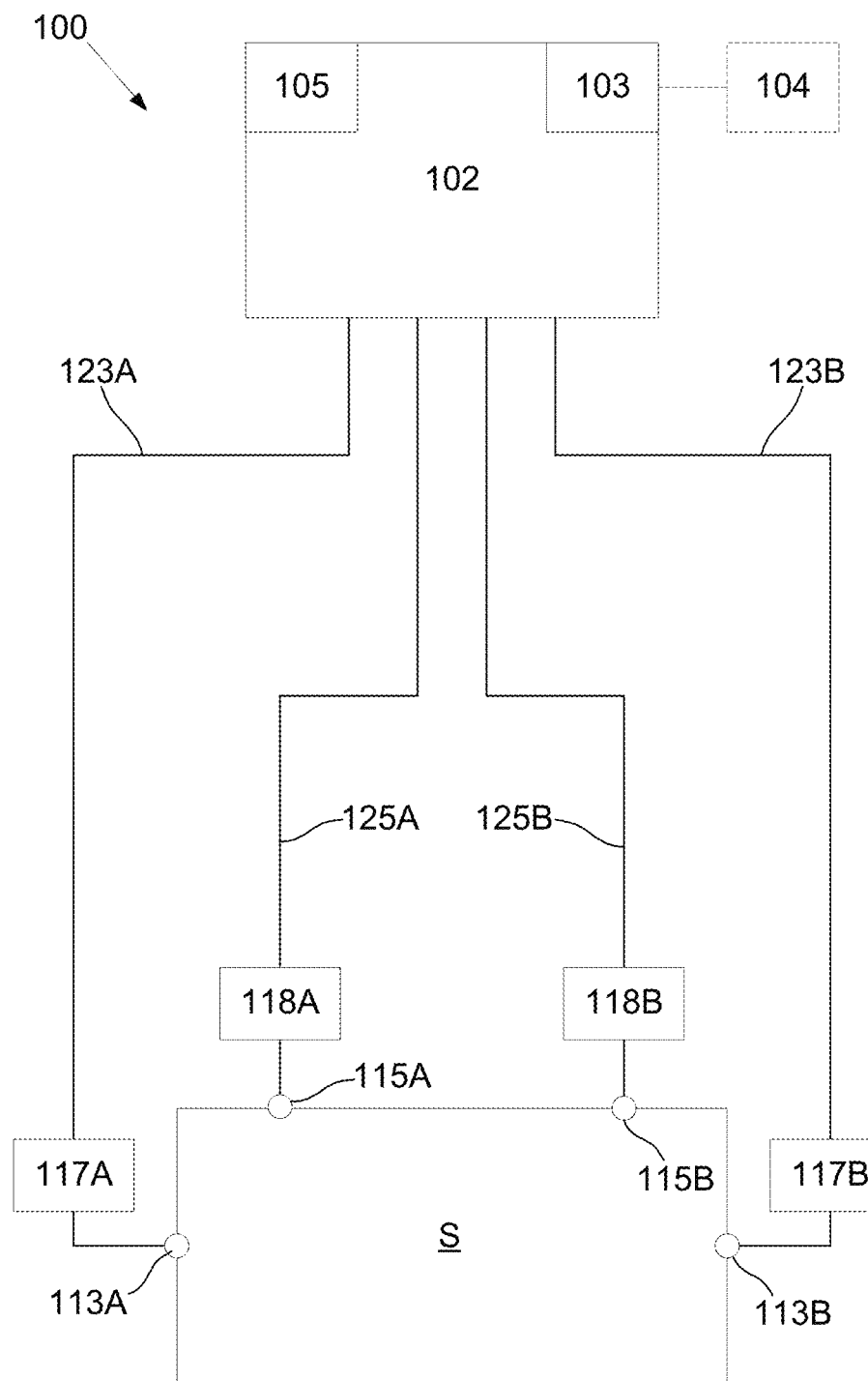
FIG. 1 is a schematic diagram of an example of an impedance determination apparatus.

An example of an apparatus suitable for performing an analysis of a subject's bioelectric impedance will now be described with reference to FIG. 1.

As shown the apparatus includes a measuring device 100 including a processing system 102, connected to one or more signal generators 117A, 117B, via respective first leads 123A, 123B, and to one or more sensors 118A, 118B, via respective second leads 125A, 125B. The connection may be via a switching device, such as a multiplexer, although this is not essential.

In use, the signal generators 117A, 117B are coupled to two first electrodes 113A, 113B, which therefore act as drive electrodes to allow signals to be applied to the subject S, whilst the one or more sensors 118A, 118B are coupled to the second electrodes 115A, 115B, which act as sense electrodes, allowing signals across the subject S to be sensed.

The signal generators 117A, 117B and the sensors 118A, 118B may be provided at any position between the processing system 102 and the electrodes 113A, 113B, 115A, 115B, and may be integrated into the measuring device 100. However, in one example, the signal generators 117A, 117B and the sensors 118A, 118B are integrated into an electrode system, or another unit provided near the subject S, with the leads 123A, 123B, 125A, 125B connecting the signal generators 117A, 117B and the sensors 118A, 118B to the processing system 102.

It will be appreciated that the above described system is a two channel device, used to perform a classical four-terminal impedance measurement, with each channel being designated by the suffixes A, B respectively. The use of a two channel device is for the purpose of example only, and multiple channel devices can alternatively be used to allow multiple body segments to be measured without requiring reattachment of electrodes. An example of such a device is described in copending patent application number WO2009059351.

An optional external interface 103 can be used to couple the measuring device 100, via wired, wireless or network connections, to one or more peripheral devices 104, such as an external database or computer system, barcode scanner, or the like. The processing system 102 will also typically include an 110 device 105, which may be of any suitable form such as a touch screen, a keypad and display, or the like.

In use, the processing system 102 is adapted to generate control signals, which cause the signal generators 117A, 117B to generate one or more alternating signals, such as voltage or current signals of an appropriate waveform, which can be applied to a subject S, via the first electrodes 113A, 113B. The sensors 118A, 118B then determine the voltage across or current through the subject S, using the second electrodes 115A, 115B and transfer appropriate signals to the processing system 102.

Accordingly, it will be appreciated that the processing system 102 may be any form of processing system which is suitable for generating appropriate control signals and at least partially interpreting the measured signals to thereby determine the subject's bioelectrical impedance, and optionally determine other information such as relative fluid levels, or the presence, absence or degree of conditions, such as oedema, lymphoedema, measures of body composition, cardiac function, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like.

In use, the first electrodes 113A, 113B are positioned on the subject to allow one or more signals to be injected into the subject S. The location of the first electrodes will depend on the segment of the subject S under study. Thus, for example, the first electrodes 113A, 113B can be placed on the thoracic and neck region of the subject S to allow the impedance of the chest cavity to be determined. Alternatively, positioning electrodes on the wrist and ankles of a subject allows the impedance of limbs, torso and/or the entire body to be determined.

Once the electrodes are positioned, one or more alternating signals are applied to the subject S, via the first leads 123A, 123B and the first electrodes 113A, 113B. The nature of the alternating signal will vary depending on the nature of the measuring device and the subsequent analysis being performed.

For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, commonly referred to as the impedance parameter value $R_0$, which is in turn indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, commonly referred to as the impedance parameter value $R_\infty$, which is in turn indicative of a combination of the extracellular and intracellular fluid levels, as will be described in more detail below.

Alternatively and/or additionally, the system can use Bioimpedance Spectroscopy (BIS) in which impedance measurements are performed at each of a number of frequencies ranging from very low frequencies (4 kHz) to higher frequencies (1000 kHz), and can use as many as 256 or more different frequencies within this range. Such measurements can be performed by applying a signal which is a superposition of a plurality of frequencies simultaneously, or a number of alternating signals at different frequencies sequentially, depending on the preferred implementation. The frequency or frequency range of the applied signals may also depend on the analysis being performed.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

A further alternative is for the system to use Multiple Frequency Bioimpedance Analysis (MFBIA) in which multiple signals, each having a respective frequency are injected into the subject S, with the measured impedances being used in the assessment of fluid levels. In one example, four frequencies can be used, with the resulting impedance measurements at each frequency being used to derive impedance parameter values, for example by fitting the measured impedance values to a Cole model, as will be described in more detail below. Alternatively, the impedance measurements at each frequency may be used individually or in combination.

Thus, the measuring device 100 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with each of the signal generators 117A, 117B being independently controllable, to allow the signal voltage across the subject to be varied.

A voltage difference and/or current is measured between the second electrodes 115A, 115B. In one example, the voltage is measured differentially, meaning that each sensor 118A, 118B is used to measure the voltage at each second electrode 115A, 115B and therefore need only measure half of the voltage as compared to a single ended system.

The acquired signal and the measured signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

As part of the above described process, the distance between the second electrodes 115A, 115B may be measured and recorded. Similarly, other parameters relating to the subject may be recorded, such as the height, weight, age, sex, health status, any interventions and the date and time on which they occurred. Other information, such as current medication, may also be recorded. This can then be used in performing further analysis of the impedance measurements, so as to allow determination of the presence, absence or degree of oedema, to assess body composition, or the like.

The accuracy of the measurement of impedance can be subject to a number of external factors. These can include, for example, the effect of capacitive coupling between the subject and the surrounding environment, the leads and the subject, the electrodes, or the like, which will vary based on factors such as lead construction, lead configuration, subject position, or the like. Additionally, there are typically variations in the impedance of the electrical connection between the electrode surface and the skin (known as the "electrode impedance"), which can depend on factors such as skin moisture levels, melanin levels, or the like. A further source of error is the presence of inductive coupling between different electrical conductors within the leads, or between the leads themselves.

Such external factors can lead to inaccuracies in the measurement process and subsequent analysis and accordingly, it is desirable to be able to reduce the impact of external factors on the measurement process.

One form of inaccuracy that can arise is caused by the voltages across the subject being unsymmetrical, a situation referred to as an "imbalance". Such a situation results in a significant signal voltage at the subject's body centre, which in turn results in stray currents arising from parasitic capacitances between the subject's torso and the support surface on which the subject is provided.

The presence of an imbalance, where the voltage across the subject is not symmetrical with respect to the effective centre of the subject, leads to a "common mode" signal, which is effectively a measure of the signal at the subject S that is unrelated to the subject's impedance, and which in turn leads to increased signal error due to capacitive losses to ground.

To help reduce this effect, it is therefore desirable for signals to be applied to the subject S so that they result in a symmetrical voltage about the subject's body centre. As a result, a reference voltage within the subject S, which is equal to a reference voltage of the measurement apparatus, will be close to the effective body centre of the subject, as considered relative to the electrode placement. As the measuring device reference voltage is typically ground, this results in the body centre of the subject S being as close to ground as possible, which minimises the overall signal magnitude across the subject's torso, thereby minimising stray currents.

In one example, a symmetrical voltage about the sensing electrodes can be achieved by using a symmetrical voltage source, such as a differential bidirectional voltage drive scheme, which applies a symmetrical voltage to each of the drive electrodes 113A, 113B. However, this is not always effective if the contact impedances for the two drive electrodes 113A, 113B are unmatched, or if the impedance of the subject S varies along the length of the subject S, which is typical in a practical environment.

In one example, the apparatus overcomes this by adjusting the differential voltage drive signals applied to each of the drive electrodes 113A, 113B, to compensate for the different electrode impedances, and thereby restore the desired symmetry of the voltages across the subject S. This process is referred to herein as balancing and in one example, helps reduce the magnitude of the common mode signal, and hence reduce current losses caused by parasitic capacitances associated with the subject.

The degree of imbalance, and hence the amount of balancing required, can be determined by monitoring the signals at the sense electrodes 115A, 115B, and then using these signals to control the signal applied to the subject via the drive electrodes 113A, 113B. In particular, the degree of imbalance can be calculated by determining an additive voltage from the voltages detected at the sense electrodes 115A, 115B.

In one example process, the voltages sensed at each of the sense electrodes 115A, 115B are used to calculate a first voltage, which is achieved by combining or adding the measured voltages. Thus, the first voltage can be an additive voltage (commonly referred to as a common mode voltage or signal) which can be determined using a differential amplifier.

In this regard, a differential amplifier is typically used to combine two sensed voltage signals $V_a$, $V_b$, to determine a second voltage, which in one example is a voltage differential $V_a-V_b$ across the points of interest on the subject S. The voltage differential is used in conjunction with a measurement of the current flow through the subject to derive impedance values. However, differential amplifiers typically also provide a "common mode" signal $(V_a+V_b)/2$, which is a measure of the common mode signal.

Whilst differential amplifiers include a common mode rejection capability, this is generally of only finite effect and typically reduces in effectiveness at higher frequencies, so a large common mode signal will produce an error signal superimposed on the differential signal.

The error caused by common mode signals can be minimised by calibration of each sensing channel. In the ideal case where both inputs of a differential amplifier are perfectly matched in gain and phase characteristics and behave linearly with signal amplitude, the common mode error will be zero. In one example, the two sensing channels of the differential amplifier are digitised before differential processing. It is therefore straightforward to apply calibration factors independently to each channel to allow the characteristics to be matched to a high degree of accuracy, thereby achieving a low common mode error.

Accordingly, by determining the common mode signal, the applied voltage signals can be adjusted, for example by adjusting the relative magnitude and/or phase of the applied signals, to thereby minimise the common mode signal and substantially eliminate any imbalance. An example of this process is described in more detail in copending patent application number WO2009059351.

Figure 2:
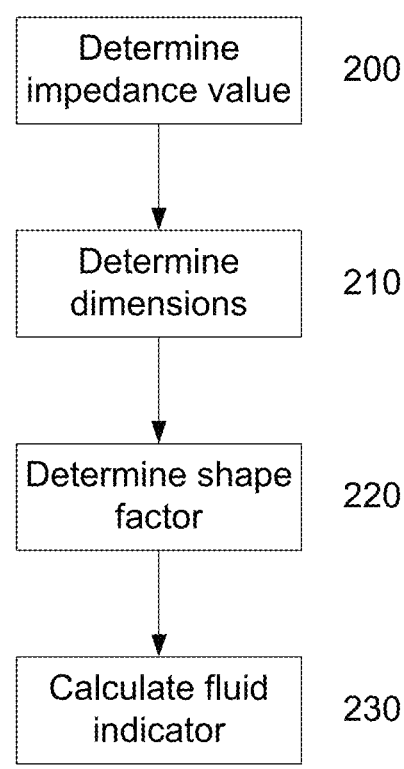
FIG. 2 is a flowchart of an example of a process for use in determining fluid levels within a subject.

An example of the operation of the apparatus in analysing impedance measurements to determine fluids levels will now be described with reference to FIG. 2. In this regard, the remainder of the specification will focus on the determination of extracellular fluid levels, but it will be appreciated that similar techniques could also be performed with respect to the determination of intracellular fluids levels, and reference to extracellular fluid levels is not therefore intended to be limiting.

In one example, the processing system 102 causes a current signal to be applied to the subject S, with the induced voltage across the subject S being measured, with signals representing the measured voltage and the applied current being returned to the processing system 102 for analysis.

When the process is being used to determine extracellular fluid levels, this is typically performed for at least a segment of the subject S that is of interest, and more typically the whole body.

It will be appreciated that the application of the current and voltage signals may be controlled by a separate processing system that is used in performing the analysis to derive an indicator, and that the use of a single processing system is for the purpose of example only.

At step 200, measured voltage and current signals are used by the processing system 102 to determine at least one impedance value at at least one frequency, the at least one impedance value representing an impedance measured for the subject. The impedance could be of one or more segments of the subject and/or of the whole body, depending on the preferred implementation, and as will be described in more detail below.

Whilst the measured impedance can be used directly, in one example, the measured impedance is used to derive an impedance parameter, and in particular an impedance (resistance) at zero frequency, $R_0$, equals the extracellular resistance $R_e$.

Figure 3A:
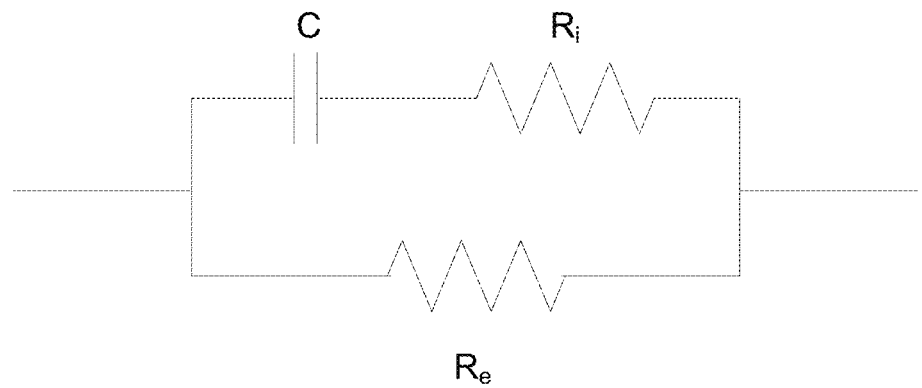
FIG. 3A is a schematic diagram of an example of a theoretical equivalent circuit for biological tissue.

In this regard, FIG. 3A is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extracellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency $R_\infty$ is given by:

$$R_\infty = \frac{R_e R_i}{R_e + R_i} \quad (1)$$

Hence the intracellular resistance is given by:

$$R_i = \frac{R_\infty R_e}{R_e - R_\infty} \quad (2)$$

Accordingly, the impedance of the equivalent circuit of FIG. 3A at an angular frequency $\omega$, where $\omega=2\pi*$frequency, is given by:

$$Z = R_\infty + \frac{R_0 - R_\infty}{1 + (j\omega\tau)} \quad (3)$$

where: $R_\infty$=impedance at infinite applied frequency
$R_0$=impedance at zero applied frequency=$R_e$ and,
$\tau$ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^\alpha} \quad (4)$$

where: $\alpha$ has a value between 0 and 1 and can be thought of as an indicator of the deviation of a real system from the ideal model.

Figure 3B:
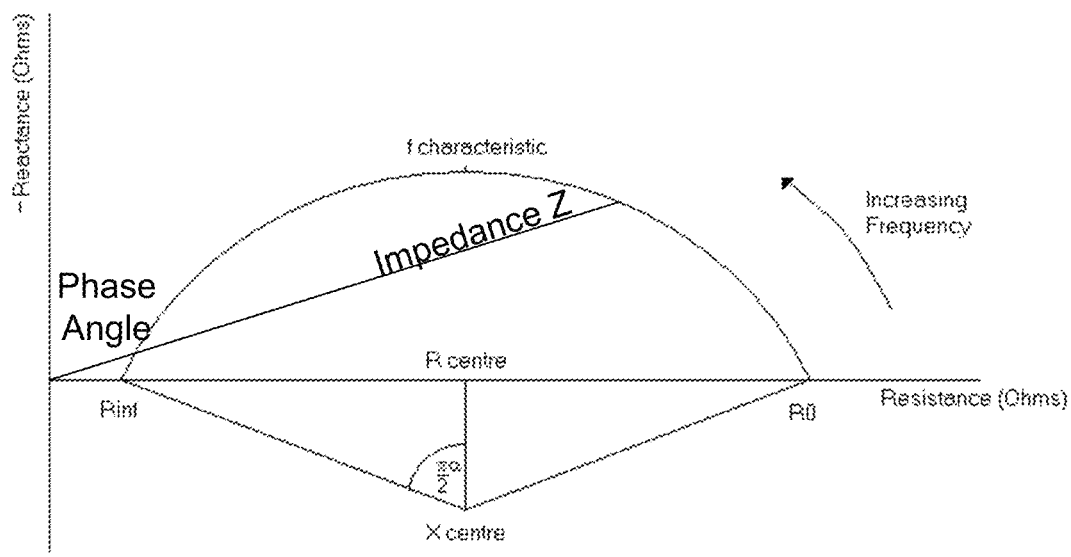
FIG. 3B is an example of a locus of impedance known as a Wessel plot.

An example of the typical multi-frequency impedance response is shown in FIG. 3B. As frequency increases, the reactance increases to a peak at the characteristic frequency and then decreases while the resistance continually decreases. This results in a circular locus with the centre of the circle below the x axis, as shown.

The values of impedance parameters $X_c$, $R_0$, $R_\infty$, $Z_c$ or $\alpha$ may be determined in any one of a number of manners such as by:
  estimating values based on impedance measurements performed at selected respective frequencies;
  solving simultaneous equations based on the impedance values determined at different frequencies;
  using iterative mathematical techniques;
  extrapolation from a plot of resistance against reactance for impedance measurements at a plurality of frequencies (a "Wessel plot" similar to that shown in FIG. 3B);
  performing a function fitting technique, such as the use of a polynomial function.

For example, the Wessel plot is often used in BIS devices, which perform multiple measurements over a range of frequencies, such as from 4 kHz to 1000 kHz, using 256 or more different frequencies within this range. A regression procedure is then used to fit the measured data to the theoretical semi-circular locus, allowing values for $X_c$, $R_0$, $R_\infty$, $Z_c$ or $\alpha$ to be calculated.

Such a regression analysis is computationally expensive, typically requiring a larger or more expensive device. The regression analysis also requires a large number of data points, which can cause the measurement process to take a significant amount of time.

Alternatively, a circle fitting technique can be used in which only three measurement points are required. In this technique, three simultaneous equations representing the geometric relationships between points on a circle are solved to allow calculation of the radius (r) and the co-ordinates of the centre of the circle (i, j) as the three parameters which define the circle. From these circle parameters, $X_c$, $R_0$, $R_\infty$, $Z_c$ or $\alpha$ are readily computed from geometric first principles.

This circle technique allows a value for $X_c$, $R_0$, $R_\infty$, $Z_c$ or $\alpha$ to be derived in a computationally less expensive manner than if a regression analysis is performed, and requires a reduced number of data points allowing a more rapid measurement process.

One potential disadvantage of the use of simultaneous equations is that if one of the impedance measurements is inaccurate for any reason, this can lead to large deviations in the calculated values of $X_c$, $R_0$, $R_\infty$, $Z_c$ or $\alpha$. Accordingly, in one example, impedance measurements are performed at more than three frequencies, with circle parameters for all possible combinations of impedance measurements at three frequencies being calculated. The average can be provided along with the standard deviation as a measure of the goodness of fit of the data to the Cole model. In the event that one of the measurements is inaccurate, this can be accounted for by excluding one or more outlier measurements, such as measurements that deviate the greatest amount from the mean, or measurements differing by more than a set number of standard deviations from the mean, allowing the mean to be recalculated, thereby providing more accurate values.

Whilst this process uses additional measurements, such as four or five measurements, this is still significantly less than the 256 or more frequencies typically performed using a BIS measurement protocol, allowing the measurement process to be performed more quickly.

In one example, the frequencies used are in the range 0 kHz to 1000 kHz, and in one specific example, four measurements are recorded at frequencies of 25 kHz, 50 kHz, 100 kHz, and 200 kHz, although any suitable measurement frequencies can be used.

A further alternative for determining impedance parameter values such as $X_c$, $R_0$, $R_\infty$, $Z_c$ or $\alpha$ is to perform impedance measurements at a single frequency, and use these as an estimate of the parameter values. In this instance, measurements performed at a single low frequency (typically less than 50 kHz) can be used to estimate $R_0$, measurements at a single high frequency (typically more than 100 kHz) can be used to estimate $R_\infty$, allowing a value of $R_i$ to be determined using equation (2) above.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

In any event, it will be appreciated that any suitable technique for determination of the parameter values such as $R_0$, $Z_c$, $R_\infty$, and $X_c$ may be used, hence allowing $R_i$ to be derived.

At step 210 physical dimensions for at least part of at least one segment of the subject are determined. The manner in which this is achieved will vary depending on the preferred implementation and could include physically measuring the dimensions of the segments of the subject, and then inputting this information into the processing system 102. However, this suffers from a number of drawbacks, including being arduous, time consuming and requiring manual entry of data, which is subject to error.

Alternatively, the dimensions could be derived from other subject parameters, such as the height, weight, sex and age of a subject, or could be determined based on dimensions measured from images of a subject, as will be described in more detail below.

At step 220, the processing system uses the dimensions to calculate a shape factor. The shape factor is used to scale the impedance measurements in order to take into account the shape of the segments of a subject, before a fluid indicator indicative of the levels of extracellular fluid is calculated at step 230.

In this regard, in the Hanai approach to body composition estimation, initial estimates of body volume and shape are very important. For a uniform conductor, such as a cylinder, resistance R is related to length H and volume V by the well-known relationship:

$$V = \frac{\rho H^2}{R} \quad (5)$$

where: $\rho$ is the resistivity of the conductor material

For a body of a different shape, a scale-independent shape factor can be used to correct the relationship:

$$V = K\frac{\rho H^2}{R} \quad (6)$$

where: K is shape factor

In the specific example of human whole body measurements, the shape factor $K_B$ accounts for the facts that the human body is not a simple cylinder and that the measurement region sampled by the electrical signal includes one arm, one leg and the trunk, but the remaining limbs and head are additional unmeasured mass. However, this is equally applicable to segmental analysis in which the shape factor Ks represents deviation in volume of the segment from a cylindrical shape.

When determining extracellular fluid levels from a measurement of the impedance, the impedance used is often that of the impedance at zero applied frequency $R_0$, in which case the resistivity in equation (6) will not be the actual resistivity of the extracellular fluid, but an apparent higher resistivity value. This is because the extracellular fluid contains a large number of non-conductive elements (cells) distributed through it. Cell walls are non-conductive at low frequencies. The apparent resistivity is given by a special case of Hanai's theory where a conductive medium contains a dispersion of particles whose resistivity is very much higher than that of the conductive medium itself:

$$\rho_{apparent} = \frac{\rho_{ecf}}{(1-c)^{3/2}} \quad (7)$$

where: c is the volume concentration of the non-conductive elements in the conductive medium.

The apparent resistivity will therefore depend on the relative concentrations of extracellular fluid and cellular material containing intracellular fluid. These are values which are not expected to be constant, so an expression which uses the true ECF resistivity is needed.

Combining equation (7) with (6) and rearranging, the expression for the extracellular fluid volume $V_{ecf}$ becomes:

$$V_{ecf} = \left(K\frac{\rho_{ecf}H^2}{R_0}\right)^{2/3} \cdot V_{WB}^{1/3} \quad (8)$$

where: $V_{WB}$ is the total body volume,
$\rho_{ecf}$ is the true resistivity of ECF For fluid levels in general, a similar equation could be used as follows:

$$V = \left(K\frac{\rho H^2}{R}\right)^{2/3} \cdot V_{WB}^{1/3} \quad (9)$$

where: V is the fluid volume
ρ is the true resistivity of the fluid
R is the impedance Usually body volume is approximated by using the subject's weight divided by a body density constant (1.05). Equation (8) is written here in a slightly different form to that generally published to make clearer how it is a development of (6).

It should be noted however that this results in assumptions regarding the fact that the extracellular fluid contains a dispersion of cells which are non-conductive at low frequencies. The extracellular fluid term and the whole body term are weighted by the powers of ⅔ and ⅓ respectively. If the distribution of non-conductive elements becomes less disperse, the values of the powers will change, so a more general equation would be:

$$V_{ecf} = \left(K_B\frac{\rho_{ecf}H^2}{R_0}\right)^{1-x} \cdot V_{WB}^{x} \quad (10)$$

where: x is a constant and typically approximately ⅓ or slightly less
$K_B$ is a whole of body shape factor
H is the subject height Similar for fluid levels more generally, this could be given by:

$$V = \left(K_B\frac{\rho H^2}{R}\right)^{1-x} \cdot V_S^{x} \quad (11)$$

where: ρ is the resistivity of the fluid
R is the impedance

For whole of body measurements, the dimensionless shape factor $K_B$ accounts for the facts that the human body is not a simple cylinder and that the measurement includes one arm, one leg and the trunk, but the remaining limbs and head are additional unmeasured mass. In one example, the shape factor for the whole body is calculated using the equation:

$$K_B = \frac{1}{H^2}\left[\left(\frac{L_l}{C_l^2} + \frac{L_t}{C_t^2} + \frac{L_a}{C_a^2}\right)(2L_aC_a^2 + 2L_lC_l^2 + 2L_tC_t^2)\right] \quad (12)$$

where: $K_B$ is the shape factor
H is the height of the subject
$L_l$ is the length of the leg
$L_t$ is the length of the torso
$L_a$ is the length of the arm
$C_l$ is the circumference of the leg
$C_t$ is the circumference of the torso
$C_a$ is the circumference of the arm Similarly, when applied to individual segments, this accounts for the fact that the segments are typically not strictly cylindrical in shape.

A provisional value for a whole body shape factor $K_B$ has been previously determined to be around 4.3, and this is generally treated as a constant. However, this value was determined from army personnel data and is not representative of the general population. In addition, not all people will necessarily have the same shape, whilst differences are likely between ethnic groups, sexes and ages. The relative body proportions also vary for subjects of different height and weight.

Using a fixed shape factor therefore relies on the assumption that all subjects have their muscle and fat mass distributed in the same way, which is known to be incorrect. Accordingly, the above described process operates by determining a personalised shape factor based on dimensions of segments of the subject.

Whilst the dimensions could be measured for a subject's limb lengths and circumferences, in practice the time involved would be prohibitive in a clinical setting. Alternatively, other techniques could be used.

In one example, this is achieved by determining subject parameters including a height, a weight, an age and a sex and determining the physical dimensions using subject parameters. Thus, in this example, the shape factor is estimated using previously determined anthropometric relationships, and each subject's height and weight, which are already measured.

Alternatively, this could be achieved by capturing at least one image of the subject and measuring the physical dimensions from the at least one image. For example, this could be performed by determining a silhouette of the subject from the at least one image and measuring the physical dimensions from the silhouette.

In one example, when performing whole of body extracellular fluid indicator measurements, this is achieved by determining a whole of body impedance measurement, determining physical dimensions for segments including at least a torso, an arm and a leg, using the physical dimensions to determine a whole body shape factor and calculating the extracellular fluid indicator at least in part using the whole of body impedance measurement and the whole body shape factor.

Figure 4:
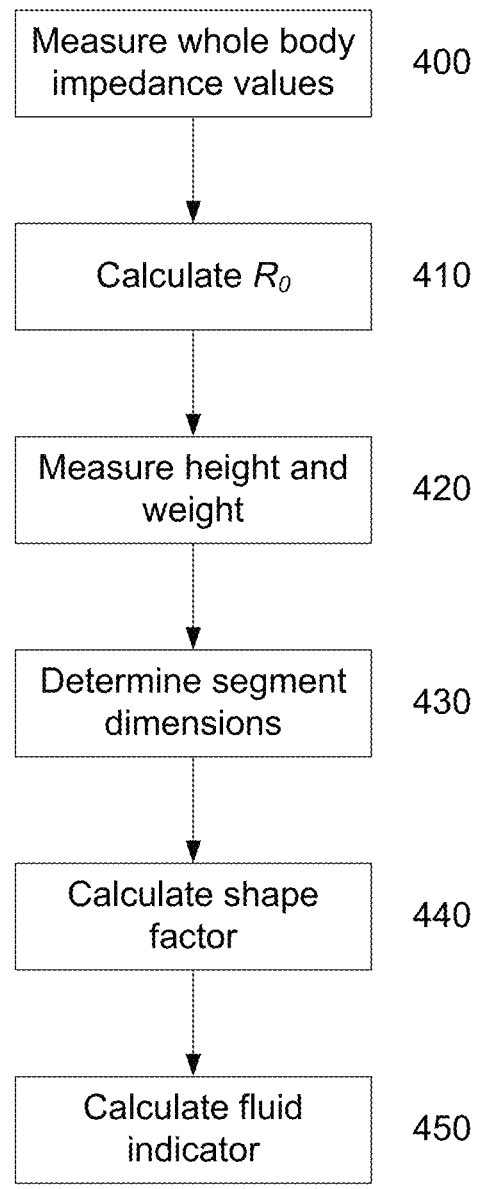
FIG. 4 is a flowchart of an example of a process for use in determining whole of body fluid levels within a subject.

A specific example of this will now be described with reference to FIG. 4.

In this example, at step 400 whole of body impedance measurements are performed at a number of different frequencies. To achieve this, an operator typically positions the electrodes 113, 115 on the subject S, and connects the leads 123, 124, 125, 126, to allow the whole body impedance measurements to be performed.

Figure 5A:
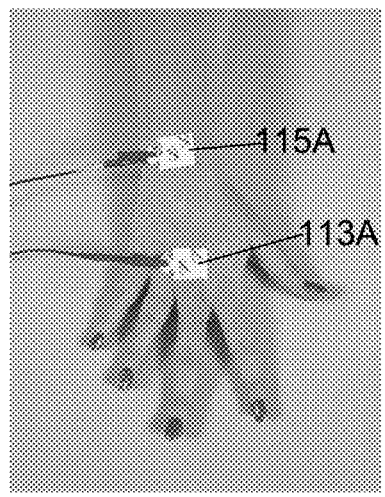
FIGS. 5A and 5B are diagrams of examples of electrode positions for use in measuring limb impedances.
Figure 5B:
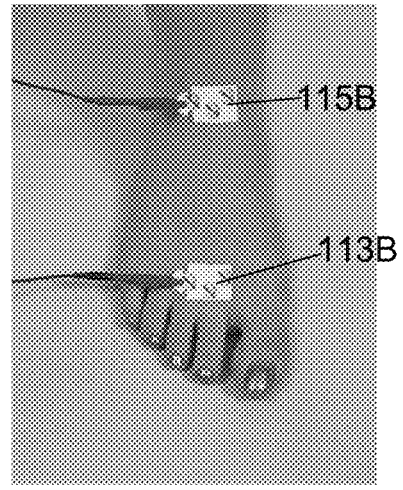
Figure 5C:
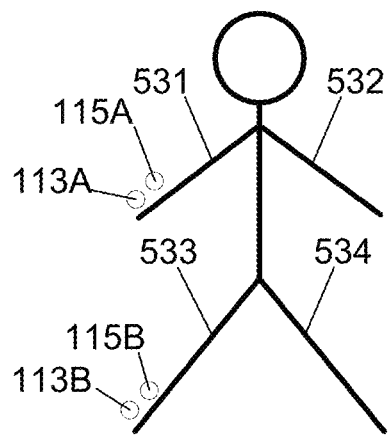
FIG. 5C is a schematic diagram of an example of electrode positions for use in measuring whole body impedance.

The general arrangement is to provide electrodes on the hand at the base of the knuckles and between the bony protuberances of the wrist, as shown in FIG. 5A, and on the feet at the base of the toes and at the front of the ankle, as shown in FIG. 5B, with the configuration shown in FIG. 5C allowing whole of body measurements to be performed. Once electrodes are positioned the operator activates the impedance measurement process, causing a sequence of drive signals to be applied to the subject at multiple frequencies. Corresponding sense signals are measured, allowing a value to be derived for the impedance parameter value $R_0$ at step 410, using the techniques previously described.

Following this, at step 420, the height and weight of the subject are measured, and provided to the processing system 102, for example using manual input techniques.

Figure 6A:
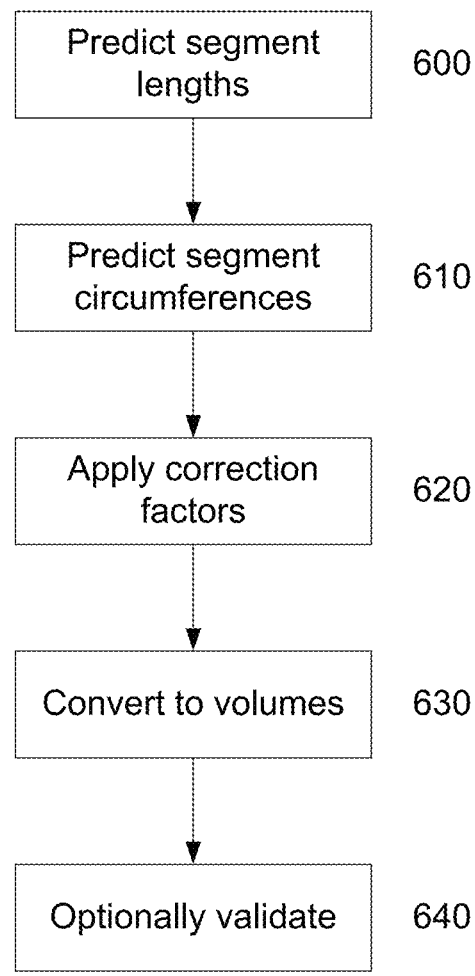
FIG. 6A is a flowchart of a first example of a process for determining segment dimensions.

Segment dimensions are then determined for the arm, torso and leg and a first example of this process will now be described with reference to FIG. 6A.

In this example, at step 600, segment lengths for each of the arm, torso and leg are predicted using known anthropometric ratios, which relate the respective segment lengths to the height of the subject.

At step 610, segment circumferences are predicted. In one example, this is achieved using the technique outlined in Heymsfield S B, Martin-Nguyen A, Fong T M, Gallagher D and Pietrobelli A 2008. Body circumferences: clinical implications emerging from a new geometric model. *Nutr. and Metab.* 5:24. This describes determined relationships between height, total body volume (approximately equivalent to weight), sex and age of subjects and the circumferences of the body segments at the upper arm, waist, hip, thigh and calf. In one example, this is given by:

$$\ln(circ) = k_0 + k_{age}\ln(\text{age}) + k_{\frac{V}{H}}\ln\left(\frac{V}{H}\right) \quad (13)$$

Where the constant coefficients are as in the table 1 below and V/H is the ratio of volume to height.

TABLE 1

|  |  | Arm | Waist | Hip | Thigh | Calf |
| --- | --- | --- | --- | --- | --- | --- |
| Male | $k_{V/H}$ | 0.61 | 0.62 | 0.42 | 0.5 | 0.38 |
|  | $k_{Age}$ | −0.052 | 0.1 | 0 | −0.1 | −0.04 |
|  | $k_0$ | 4.2 | 4.63 | 4.96 | 4.8 | 4.1 |
| Female | $k_{V/H}$ | 0.62 | 0.61 | 0.49 | 0.54 | 0.33 |
|  | $k_{Age}$ | 0.024 | 0.064 | 0 | −0.032 | −0.046 |
|  | $k_0$ | 3.88 | 4.68 | 5.06 | 4.65 | 4.07 |

Following determination of circumferences, correction factors are applied at step 620, to convert the segmental circumference to an equivalent cylindrical circumference. This is the circumference of a cylinder the same length as the body segment, and which has the same volume as the body segment. The correction factor will typically depend on factors such as sex, age or other parameters, and can be determined through analysis of a sample reference population.

Following this, volumes for the segments can be determined at step 630, with these optionally being validated at step 640 by calculating a volume error, using the subject weight and allowing for the head, hands and feet which are not included in the segments. A further test at this stage is to plot volume error against the shape factor $K_b$. If the prediction algorithms apply the wrong proportion of weight or volume to the different body segments, this is likely to lead to a $K_B$ error which is correlated with a volume error.

Figure 6B:
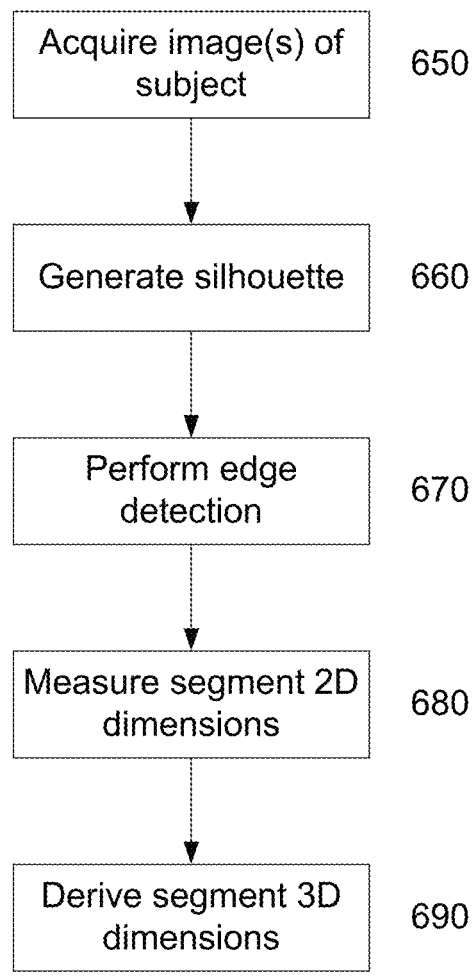
FIG. 6B is a flowchart of a second example of a process for determining segment dimensions.

As an alternative approach, shown in FIG. 6B, one or more images of the subject can be acquired at step 650. This can be achieved by taking a photograph of the subject, or alternatively could be performed using other imaging modalities, such as DEXA (Dual-Energy X-ray Absorptiometry), 3D laser or optical scanning, or the like.

At step 660, a silhouette is generated from the image(s), with edge detection and/or pattern recognition to be used to identify one or more landmarks, at step 670. The landmarks correspond to defined locations on the body, which are used to derive 2D dimensions, which can then be extrapolated to 3D dimensions, including circumferences.

As part of this process the circumferences are then used to determine volumes, as in the previous example, allowing shape factors to be determined. As part of this process, multiple circumferences could be determined, for example by making multiple measurements along each body segment, allowing the volume to be more accurately determined, for example by integrating the circumferences along the length of the body segment.

Once dimensions have been determined, at step 440 this allows a body shape factor to be determined, using the equation (12) outlined above. Following this, at step 450, the processing system 450 can determine an extracellular fluid indicator using the equations (7) or (8).

Thus, the above described technique allows body composition estimates to be made using a personalised $K_B$ value.

Figure 7:
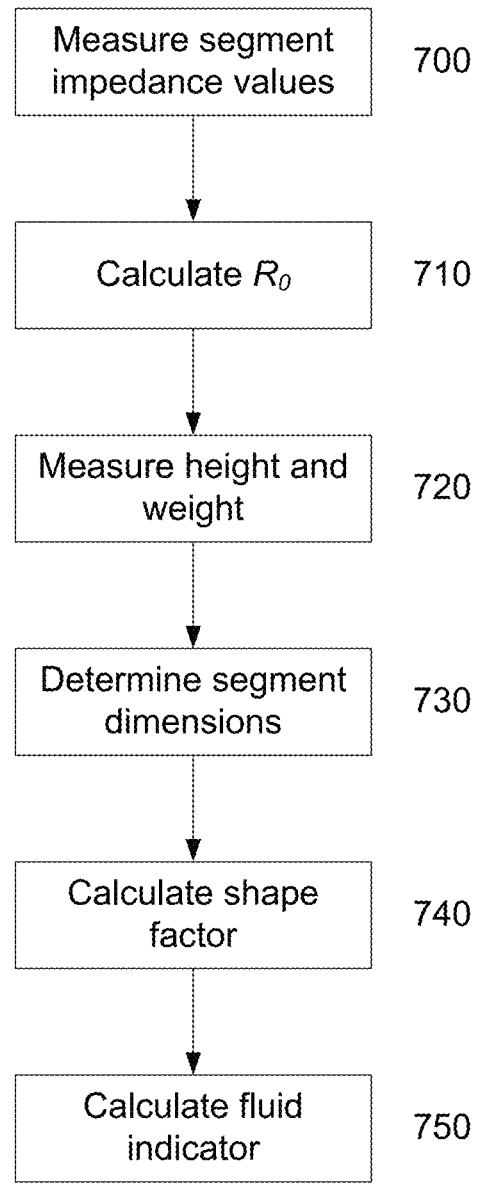
FIG. 7 is a flowchart of an example of a process for use in determining segmental fluid levels within a subject.

It will be appreciated that whilst the above described example has focused on the application to whole body extracellular measurements, similar techniques could also be applied to segmental extracellular fluid measurements. In this example, the approach typically includes determining a segmental impedance measurement for at least one segment, determining physical dimensions for the at least one segment, using the physical dimensions to determine a segmental shape factor and calculating the extracellular fluid indicator at least in part using the segmental impedance measurement and the segmental shape factor. An example of this will now be described with reference to FIG. 7.

In this example, at step 700 segmental impedance measurements are performed at a number of different frequencies on one or more body segments. To achieve this, an operator typically positions the electrodes 113, 115 on the subject S, and connects the leads 123, 124, 125, 126, to allow the whole body impedance measurements to be performed.

Figure 8A:
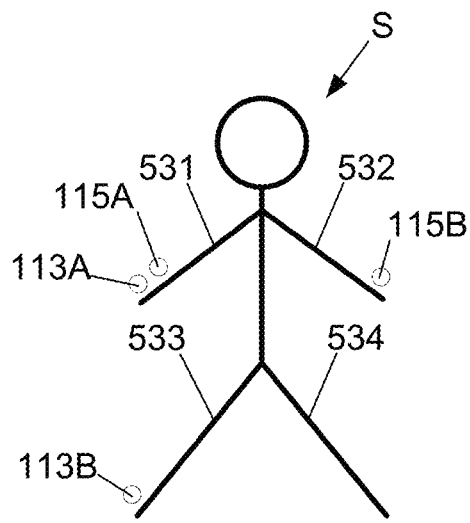
FIGS. 8A and 8B are schematic diagrams of examples of electrode positions for use in measuring limb impedances; and,
FIG. 8C is a schematic diagram of an example of electrode positions for use in measuring a body segment impedance.
Figure 8B:
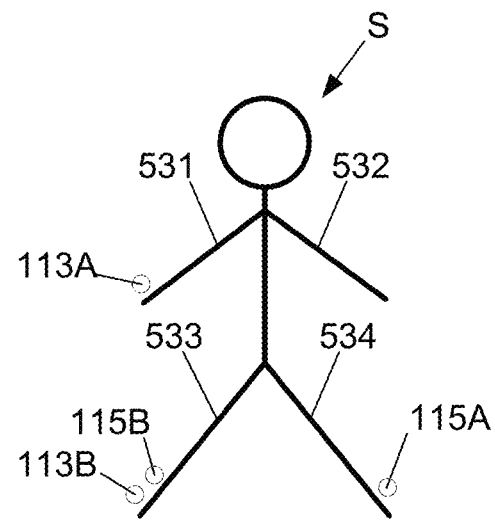

As before, this will include providing electrodes on the hand at the base of the knuckles and between the bony protuberances of the wrist, as shown in FIG. 5A, and on the feet at the base of the toes and at the front of the ankle, as shown in FIG. 5B. In this example, the arrangements shown in FIGS. 8A and 8B are used to allow the right arm 531 and the right leg 533 to be measured respectively. It will be appreciated that this configuration uses the theory of equal potentials, allowing the electrode positions to provide reproducible results for impedance measurements. For example when current is injected between electrodes 113A and 113B in FIG. 8A, the electrode 115B could be placed anywhere along the left arm 532, since the whole arm is at an equal potential. This is advantageous as it greatly reduces the variations in measurements caused by poor placement of the electrodes by the operator. It also greatly reduces the number of electrodes required to perform segmental body measurements, as well as allowing the limited connections shown to be used to measure each limb separately. However, it will be appreciated that any suitable electrode and lead arrangement may be used.

Figure 8C:
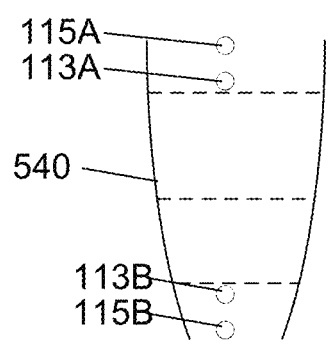

For example, any suitable segment of the subject can be measured, using the electrode arrangement shown in FIG. 8C, with electrodes position at either end of the relevant body segment.

At step 710, the impedance parameter value $R_0$ is calculated for each body segment, before the subject's height and weight are determined and provided to the processing system 102 at step 720. Segment dimensions are then determined at step 730, using techniques similar to those outlined above with respect to FIGS. 6A and 6B, before a shape factor is determined for each segment. This can be performed in a manner similar to that outlined above with respect to the body segment, and can include converting individual circumferences into volume circumferences. Following this, individual extracellular fluid indicators can be determined for each measured segment at step 750, using the following equation:

$$SV_{ecf} = \left(K_S \frac{\rho_{ecf} L^2}{R_0}\right)^{1-x} \cdot V_S^x \qquad (14)$$

where: $SV_{ecf}$ is the segmental extracellular fluid volume
$K_S$ is the segmental shape factor
$V_S$ is the segment volume
$\rho_{ecf}$ is the resistivity of extracellular fluid
L is the segment length
$R_0$ is the impedance at zero frequency
x is a constant
Similar for fluid levels more generally, this could be given by:

$$SV = \left(K_S \frac{\rho L^2}{R}\right)^{1-x} \cdot V_S^x \qquad (15)$$

where: SV is the segmental fluid volume
$\rho$ is the resistivity of the fluid
R is the impedance Thus, the above described technique allows body composition estimates to be made using a personalised shape factor, either for the entire body, or for individual body segments.

The above described techniques have been used to determine shape factors for a range of different individuals, with preliminary values resulting in body shape factor $K_B$ values in the range of 4.0 to 4.4, in particular averaging about 4.0 for females and between 4.0 for young males and increasing to around 4.4 as age increases. This generally agrees with prior studies but highlights significant differences based on at least age and sex, highlighting the importance of using personalised shape factors.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method for use in determining fluid levels within a subject, the method including, in a processing device that is configured to:
    a) determine at least one impedance value measured for the subject, wherein the at least one impedance values are measured by applying one or more drive signals to the subject using a first set of electrodes and measuring one or more sense electrical signals across a second set of electrodes applied to the subject;
    b) determine physical dimensions for at least part of at least one segment of the subject;
    c) use the physical dimensions to determine a shape factor at least partially indicative of a shape of the at least one segment; and,
    d) calculate a fluid indicator indicative of the fluid levels in the segment at least in part using the at least one impedance value and the shape factor;
        wherein the physical dimensions are measured for the subject by:
        i) capturing at least one image of the subject;
        ii) determining a silhouette of the subject from the at least one image; and
        iii) measuring the physical dimensions from the silhouette.

2. A method according to claim 1, wherein the method includes, in a processing device that is being configured to:
    a) determine an impedance parameter value using the impedance value measured, the impedance parameter value being indicative of an impedance at zero frequency; and,
    b) calculate the fluid indicator using the impedance parameter value.

3. A method according to claim 2, wherein the method includes, in a processing device that is being configured to:
    a) determine a number of impedance measurements, the number of impedance measurements including at least one impedance measurement at each of a number of measurement frequencies; and,
    b) determine the impedance parameter value using the number of impedance measurements.

4. A method according to claim 1, wherein the physical dimensions include a length and circumference of the at least one segment.

5. A method according to claim 1, wherein the method includes, in a processing device that is configured to, determine a whole of body fluid indicator by:
    a) determining a whole of body impedance measurement;
    b) determining physical dimensions for segments including at least:
        i) a torso;
        ii) an arm; and,
        iii) a leg;
    c) using the physical dimensions to determine a whole body shape factor; and,
    d) calculating the fluid indicator at least in part using the whole of body impedance measurement and the whole body shape factor.

6. A method according to claim 1, wherein the method includes, in a processing device that is configured to, determine a segmental fluid indicator indicative of a fluid volume of the at least one segment by:
    a) determining a segmental impedance measurement for the at least one segment;
    b) determining physical dimensions for the at least one segment;
    c) using the physical dimensions to determine a segmental shape factor; and,
    d) calculating the fluid indicator at least in part using the segmental impedance measurement and the segmental shape factor.

7. A method according to claim 1, wherein the fluid indicator is indicative of at least one of:
    a) extracellular fluid levels; and,
    b) intracellular fluid levels.

8. A method according to claim 1, wherein the method includes, in the processing device that is configured to:
  a) cause at least one drive signal to be applied to the subject using a signal generator;
  b) determine at least one sense signal measured across the subject using a sensor; and,
  c) determine at least one impedance value using an indication of the drive signal and the sensed signal.

9. Apparatus for use in measuring fluid levels within a subject, the apparatus including:
  a) a signal generator that is configured to apply one or more drive signals to the subject using a first set of electrodes;
  b) a sensor that is configured to measure one or more sense electrical signals across a second set of electrodes applied to the subject; and,
  c) a processing device that is configured to:
    i) determine at least one impedance value measured for the subject using the drive and sense electrical signals;
    ii) determine physical dimensions for at least part of at least one segment of the subject;
    iii) use the physical dimensions to determine a shape factor at least partially indicative of a shape of the at least one segment; and,
    iv) calculate a fluid indicator indicative of the fluid levels in the segment at least in part using the at least one impedance value and the shape factor;
  wherein the physical dimensions are measured for the subject by the processor that is configured to:
    (1) capture at least one image of the subject;
    (2) determine a silhouette of the subject from the at least one image; and
    (1) measure the physical dimensions from the silhouette.

* * * * *